(12) United States Patent
Brinker et al.

(10) Patent No.: US 10,517,560 B2
(45) Date of Patent: Dec. 31, 2019

(54) METHOD AND MEDICAL IMAGING APPARATUS FOR DETERMINING AT LEAST ONE PATIENT-SPECIFIC SAFETY PARAMETER FOR A MEDICAL IMAGING EXAMINATION

(71) Applicant: Siemens Healthcare GmbH, Erlangen (DE)

(72) Inventors: Gerhard Brinker, Erlangen (DE); Anja Jaeger, Fuerth (DE); Daniel Niederloehner, Erlangen (DE); Stephan Nufer, Erlangen (DE); Jens Thoene, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 785 days.

(21) Appl. No.: 15/193,823

(22) Filed: Jun. 27, 2016

(65) Prior Publication Data

US 2017/0000446 A1 Jan. 5, 2017

(30) Foreign Application Priority Data

Jun. 30, 2015 (DE) .................... 10 2015 212 206

(51) Int. Cl.
*A61B 6/00* (2006.01)
*A61B 5/11* (2006.01)
*A61B 6/03* (2006.01)

(52) U.S. Cl.
CPC ............. *A61B 6/544* (2013.01); *A61B 5/1128* (2013.01); *A61B 6/032* (2013.01); *A61B 6/037* (2013.01)

(58) Field of Classification Search
CPC .... G16H 40/63; G01R 33/543; G01R 33/288; A61B 5/1128; A61B 5/055; A61B 6/544; A61B 6/04; A61B 6/107; A61B 6/032; A61B 6/037
See application file for complete search history.

(56) References Cited

U.S. PATENT DOCUMENTS

| 2002/0118280 | A1 | 8/2002 | Medlar et al. |
| 2003/0098687 | A1* | 5/2003 | Arneth ................ A61B 5/055 324/309 |
| 2006/0197528 | A1* | 9/2006 | Bielmeier .............. G01R 33/28 324/314 |
| 2010/0303205 | A1 | 12/2010 | Kapoor et al. |
| 2013/0083894 | A1* | 4/2013 | Niebler ................ A61B 6/4441 378/62 |

(Continued)

FOREIGN PATENT DOCUMENTS

| CN | 103767722 A | 5/2014 |
| DE | 102011084444 A1 | 4/2013 |

*Primary Examiner* — Bo Joseph Peng
(74) *Attorney, Agent, or Firm* — Schiff Hardin LLP

(57) ABSTRACT

In a method and apparatus for determining at least one patient-specific safety parameter for a medical imaging examination conducted on the patient by a medical imaging device, position data of the patient are acquired by a position data detector while the patient is on a patient-positioning device of the medical imaging apparatus. The acquired position data are evaluated in a processor in order to determine position information of the patient. The patient-specific safety parameter is determined using the position information of the patient.

16 Claims, 2 Drawing Sheets

(56) References Cited

U.S. PATENT DOCUMENTS

| | | | |
|---|---|---|---|
| 2013/0298329 A1* | 11/2013 | Eder | A61G 13/121 5/601 |
| 2013/0317343 A1* | 11/2013 | Klimenko | A61B 5/055 600/411 |
| 2015/0002149 A1* | 1/2015 | Nehrke | G01R 33/243 324/309 |
| 2015/0046137 A1 | 2/2015 | Zeilinger | |
| 2015/0265852 A1 | 9/2015 | Meir et al. | |

* cited by examiner

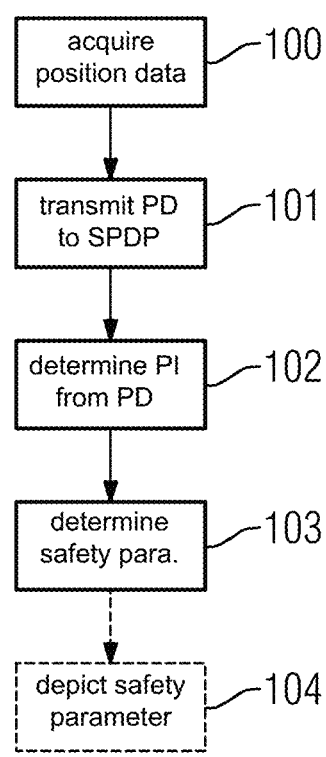

METHOD AND MEDICAL IMAGING APPARATUS FOR DETERMINING AT LEAST ONE PATIENT-SPECIFIC SAFETY PARAMETER FOR A MEDICAL IMAGING EXAMINATION

BACKGROUND OF THE INVENTION

Field of the Invention

The present invention concerns a method for determining at least one patient-specific safety parameter for a medical imaging examination on the patient, wherein the medical imaging examination is carried out by a medical imaging apparatus. The present invention also concerns a medical imaging apparatus having a scanner designed to acquire medical image data, a position-detecting unit and a safety parameter determining processor.

Description of the Prior Art

Before a medical imaging examination begins, for example a magnetic resonance examination, it is necessary for different patient parameters, such as a patient's height and/or a patient's weight, to be acquired. By means of these patient parameters, patient-specific safety parameters, such as a specific absorption rate (SAR), are determined for the pending medical imaging examination.

Conventionally, determination of the patient-specific safety parameter has been based on a cylinder model, with one cylinder respectively representing each region of the body, such as, for example, the head, the torso, etc. here.

SUMMARY OF THE INVENTION

An object of the present invention is to provide simple and precise determination of patient-specific safety parameters for a medical imaging examination on a patient.

The invention encompasses a method for determining at least one patient-specific safety parameter for a medical imaging examination on a patient, wherein the medical imaging examination is carried out by a medical imaging apparatus, having the following steps.

Position data of the patient are acquired with a position data acquisition detector. For this purpose the patient is positioned on a patient-positioning device of the medical imaging apparatus.

The acquired position data are transmitted to a safety parameter determining processor.

Position information of the patient is determined by the safety parameter determining processor using the acquired position data.

A patient-specific safety parameter is determined, using the position information of the patient, by the safety parameter determining processor.

As used herein, a patient-specific safety parameter means a safety parameter that embodies a safety value as a function of the patient-specific data, such as the patient's height, the patient's position, the patient's weight, etc. The safety parameter is a parameter relevant to the safety of the patient during the medical imaging examination. The patient-specific safety parameter can be, for example, a specific absorption rate and/or heat radiation during the medical imaging examination on the patient and/or a collision probability of the patient with the enclosure (wall surface) of the scanner during the medical imaging examination, etc.

The position data acquisition detector preferably is a camera, for example a 2D camera or a 3D camera. The medical imaging apparatus can be a magnetic resonance apparatus or a computed tomography apparatus or a PET (Positron Emission Tomography) apparatus, etc.

The ascertained position information can be, for example, a position of the patient on the patient-positioning device and/or an orientation of the patient on the patient-positioning device and/or an exact position of the patient on the patient-positioning device and/or a surface image of the patient. Furthermore, the position information of the patient can include a patient model. The position information can be determined using position data of a portion of the patient to be examined. Alternatively, the position information can also be determined using position data from the entirety of the patient, so exact determination of patient-specific safety parameters, such as determination of a specific absorption rate and/or heat radiation during the medical imaging examination on the patient, is possible.

The present invention enables particularly simple and optimally precise determination of patient-specific safety parameters, for example a specific absorption rate and/or heat radiation during the medical imaging examination on the patient and/or a collision probability of the patient during the medical imaging examination etc., for a pending medical imaging device. This advantageously increases the safety of the patient during the medical imaging examination.

Due to the position information that is incorporated in the patient-specific safety parameter, the medical imaging examination can be configured more efficiently and more safely because particularly precise position information for determining the patient-specific safety parameter is available, thereby enabling particularly precise planning of the medical imaging examination. The medical imaging examination can be planned so as to be precise in terms of voxels, and a time-optimized examination protocol can be provided for the medical imaging examination thereby. The scanning time of the medical imaging examination can be reduced as a result. This in turn contributes to the protection and/or well-being of the patient during the medical imaging examination. In particular, an examination procedure when examining children can be specifically adapted to the height and/or position of the children, and the examination time reduced thereby.

The operator of the imaging apparatus can also be assisted during the medical imaging examination because additional items of advice and/or instructions, in particular automated items of advice or instructions, can be displayed for the operator and/or depicted, due to the patient-specific safety parameter.

As noted, the position information can be a patient model, which is used to determine the patient-specific safety parameter by the safety parameter determining processor. This enables particularly precise determination of the position information of the patient on the patient-positioning device. The patient model can be adapted very precisely to the actual anatomy of the patient due to the determination of the patient model using the acquired position data, and so the patient-specific safety parameter ascertained therefrom can also be determined very precisely. The patient model is preferably determined and/or calculated by means of suitable image processing models.

In a further embodiment of the invention, the patient model is determined as an Active Shape Model and/or a cylinder model. An Active Shape Model (ASM) means a model that has multiple mutually connected points, with these points describing a shape and/or a profile and/or surface of the patient. For determining the surface of the patient in the position data, first an average shape and/or an average profile is incorporated in the position data and then individual points of the model are iteratively dragged to form edges in the surface image. Alternatively or additionally, the patient model can be determined as a cylinder model, with the cylinder model being fitted into the surface image and iteratively adapted. As a result of this embodiment of the invention the patient model can be approximated precisely and in a time-saving manner to the patient's anatomy, so position information adapted to reality is available for further determination of the patient-specific safety parameter.

If the at least one patient-specific safety parameter includes or is a specific absorption rate for the medical imaging examination, the duration of the examination can be optimized because the specific absorption rate can be determined accurately for the pending medical imaging examination due to the position data of the patient. The specific absorption rate is a measure of how strongly the patient has been radiated with RF energy during a magnetic resonance imaging examination, which makes use of RF pulses during the medical imaging examination. The specific absorption rate is based on limit values that, in the event of the specific absorption rate potentially being exceeded, lead to the insertion of non-radiating intervals in the scan, and thereby a lengthening of the scanning time.

In a further embodiment of the invention, the at least one patient-specific safety parameter includes or is heat radiation on the patient during the medical imaging examination. The patient thus can be protected against excessive heat exposure during the medical imaging examination and the safety of the patient can be increased thereby. Excessive heat radiation can occur, for example, when the distance between the patient and a surface of the scanner is too small and/or with an excessively long period of irradiation and/or excessively high irradiation energy.

In a further embodiment of the invention, the at least one patient-specific safety parameter includes or is a collision probability of the patient with the enclosure of the patient-receiving region of the scanner. In this way the safety of the patient during the medical imaging examination can advantageously be increased.

A value of the at least one patient-specific safety parameter can be depicted at a display monitor, so a user and/or a medical operator can obtain information and/or monitor the patient-specific safety parameter. The user thus can be informed directly about adherence to patient-specific safety parameters, such as a collision probability and/or heat radiation.

In a further embodiment of the invention, at least one work instruction and/or an item of advice is depicted at a display monitor. In this way additional information, which is present due to the acquired position data and/or the ascertained position information and/or the ascertained patient-specific safety parameter within the safety parameter determining unit, can be displayed for a user. For example, situation information and/or position information and/or the patient-specific safety parameter can be communicated to the user. In particular, when a patient-specific safety parameter is exceeded beyond a predefined limit value the user can receive an instruction that can include, for example, an interruption to the medical imaging examination and/or a correction of a patient position, so adherence to limit values for the patient-specific safety parameter can be ensured.

The invention also encompasses a medical imaging apparatus having a data acquisition scanner, a position-detecting detector and a safety parameter determining processor, wherein the medical imaging apparatus is designed to implement the method according to the invention for determining at least one safety parameter for a medical imaging examination on the patient of a patient, as described above.

This enables particularly simple and optimally precise determination of patient-specific safety parameters, for example a specific absorption rate and/or heat radiation during the medical imaging examination on the patient and/or a collision probability of the patient during the medical imaging examination etc., for a pending medical imaging device. Furthermore, this increases the safety of the patient during the medical imaging examination.

The medical imaging examination can be configured more efficiently and more safely due to the position information, which is incorporated in the patient-specific safety parameter, since very precise position information for determination of the patient-specific safety parameter is used and this enables particularly exact planning of the medical imaging examination. The medical imaging examination can be planned so as to be precise in terms of voxels, and a time-optimized examination protocol can therefore be supplied for the medical imaging examination. The scanning time of the medical imaging examination can be reduced as a result. This in turn contributes to the protection and/or well-being of the patient during the medical imaging examination. In particular, an examination procedure when examining children can be specifically adapted to the height and/or position of the children and an examination time reduced thereby.

The medical apparatus operator can also be assisted during the medical imaging examination because additional items of advice and/or instructions, in particular automated items of advice or instructions, can be displayed and/or depicted for the user due to the patient-specific safety parameter.

The advantages of the inventive medical imaging apparatus correspond to the advantages of the inventive method for determining at least one patient-specific safety parameter for a medical imaging examination on the patient, as have been stated above in detail. Features, advantages or alternative embodiments mentioned in this connection are applicable to the inventive apparatus as well.

The position data acquisition detector can be at least one camera that is arranged inside the patient-receiving region that is at least partially surrounded by the scanner. This enables simple detection of position data of the patient with respect to a dimension and/or size of the patient-receiving region. An image of an empty patient-receiving region can be supplied hereby, wherein the empty patient-receiving region is patient-free. This can be compared with the position data of the patient, so protection against contact with a surface of the patient-receiving region can be provided for the patient. A collision probability is determined by the safety parameter determining processor using the position data of the patient and the image data of the patient-receiving region.

In a further embodiment of the invention the position data acquisition detector is at least one camera that is arranged outside of a patient-receiving region that is at least partially surrounded by the scanner. This enables detection of the patient on the patient-positioning device while position data of a region of the body to be examined, or even the entire patient, are detected. Particularly simple and inexpensive detection of position data can be achieved if the position data acquisition detector is at least one 2D camera and/or at least one 3D camera.

The invention also encompasses a non-transitory, computer-readable data storage medium that can be loaded directly into a memory of a programmable system control computer of a medical imaging apparatus. The storage medium is encoded with programming instructions s(program code) that cause the computer to implement the method for determining at least one patient-specific safety parameter for a medical imaging examination on the patient in accordance with the invention when the program code is executed in the system control computer. The programming instructions require program means such as libraries and help functions, to implement the corresponding embodiments of the method. The program code can be a source code that has still to be compiled and embedded or that only has to be interpreted, or an executable software code that for execution, then only has to be loaded in the computer.

BRIEF DESCRIPTION OF THE DRAWINGS

FIG. 2 is a flowchart of an embodiment of the inventive method for determining at least one patient-specific safety parameter for a medical imaging examination on a patient.

DESCRIPTION OF THE PREFERRED EMBODIMENTS

Figure 1:
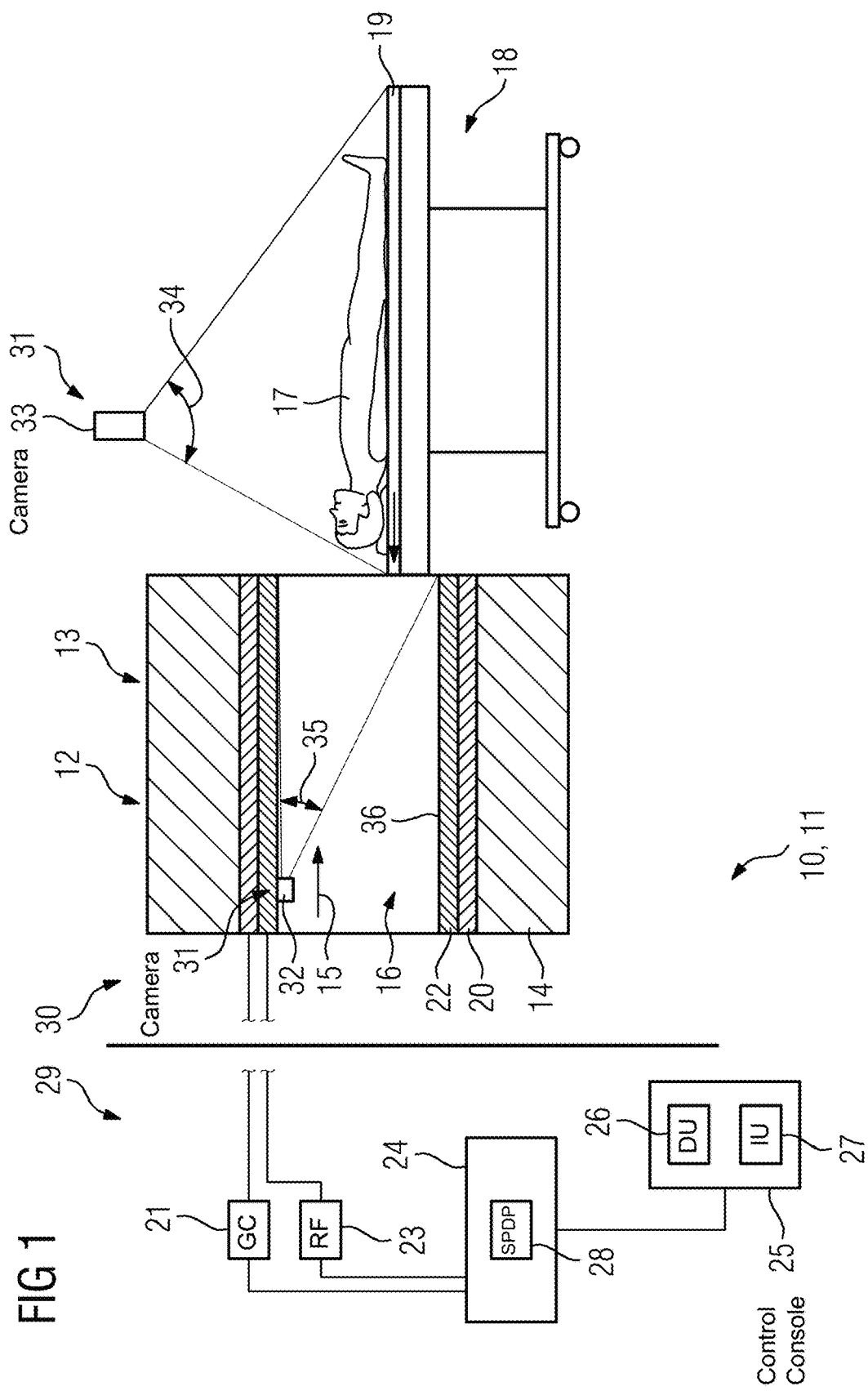
FIG. 1 schematically illustrates an inventive medical imaging apparatus.

FIG. 1 schematically depicts a medical imaging apparatus 10. In the exemplary embodiment the medical imaging apparatus 10 is formed as a magnetic resonance apparatus. The embodiment of the medical imaging apparatus 10 is not limited to a magnetic resonance apparatus, however. The medical imaging apparatus 10 can be any medical imaging apparatus that is considered reasonable to those skilled in the art, such as, for example, a computed tomography apparatus, a positron emission tomography apparatus, a C-arm device, etc.

The apparatus 10 in the form of a magnetic resonance apparatus comprises a data acquisition scanner 13, formed by a magnet unit. The magnet unit of the scanner 13 has a superconductive basic field magnet 14 for generating a strong and constant basic magnetic field 15. In addition the scanner 13 has a patient-receiving region 16 for receiving a patient 17. In the exemplary embodiment the patient-receiving region 16 is cylindrical and cylindrically surrounded in the circumferential direction by the scanner 13. A different design of the patient-receiving region 16 is conceivable. The patient 17 can be moved by a patient-positioning device 18 into the patient-receiving region 16. The patient-positioning device 18 has for this purpose an examination table 19 designed to move within the patient-receiving region 16.

The scanner also has a gradient coil arrangement 20 for generating magnetic field gradients that are used for spatial encoding during imaging. The gradient coil arrangement 20 is controlled by means of a gradient control processor 21 of the magnetic resonance apparatus. The scanner 13 also has a radio-frequency (RF) antenna 22 for exciting nuclear spins of the patient 17. So as to deviate from the polarization that is established in the basic magnetic field 15. The radio-frequency antenna 22 is controlled by a radio-frequency antenna control processor 23 and radiates radio-frequency magnetic resonance sequences into the patient-receiving region 15 of the scanner 13.

For controlling the basic field magnet 14 the gradient control processor 21 and the radio-frequency antenna control processor 23, the magnetic resonance apparatus has a system control computer 24. The system control computer 24 centrally controls the magnetic resonance apparatus, such as to execute a predetermined imaging gradient echo sequence. Furthermore, the system control computer 24 has an evaluation processor (not shown) for evaluation of medical image data that are acquired during the magnetic resonance examination. The magnetic resonance apparatus also has a control console 25 that is connected to the system control computer 24. Control information, such as, for example, imaging parameters, and reconstructed magnetic resonance images, can be displayed on a depiction unit 26, for example on at least one monitor, of the control console 25 for a user, such as a medical operator. The control console 25 also has an input unit 27 via which information and/or parameters can be entered by the medical operator during a scanning process.

The system control computer 24 has, in accordance with the invention, a safety parameter determining processor 28. The system control computer 24 also has a memory (not shown) and a main processor (not shown).

The system control computer 24 is arranged together with the control console 25, gradient control processor 21 and radio-frequency antenna control processor 23 inside a control room 29. The scanner 13 is situated inside an examination room 30, with the examination room 30 preferably being shielded outwardly and inwardly in order to shield against disruptive effects that can affect a medical imaging examination and be caused by the medical imaging apparatus 10. The examination room 30, in an embodiment of the medical imaging apparatus 10 as a magnetic apparatus, is shielded with respect to magnetic fields as well as against electromagnetic radiation, in particular radio-frequency radiation.

The medical imaging apparatus 10 (the magnetic resonance apparatus) also has a position-detecting detector 31 that is inside the examination room 30. The position-detecting detector 31 comprises a first camera 32 which is arranged inside the patient-receiving region 16. The first camera 32 has an acquisition region 35 that covers an insertion opening of the patient-receiving region 16.

The position-detector 31 also has a second camera 33 situated outside of the patient-receiving region 16. The second camera 33 is preferably arranged on a ceiling of the examination room 30, such that an acquisition region 34 of the second camera 33 is directed toward a region that adjoins the front of the medical imaging apparatus 10.

The acquisition regions 34, 35 of the first camera 32 and the second camera 33 are regions within which acquisition of camera data, in particular position data, can be acquired. In the exemplary embodiment, the first camera 32 and the second camera 33 are each formed by a 2D camera and/or a 3D camera.

In an alternative embodiment of the invention, the position-detector 31 can have just one camera, or more than two cameras.

FIG. 2 shows a sequence of an inventive method for determining at least one patient-specific safety parameter for a medical imaging examination on a patient 17. The medical imaging examination is implemented by the medical imaging apparatus 10, in the exemplary embodiment by the magnetic resonance apparatus. The method is controlled and implemented by the safety parameter determining processor 28. For this purpose the safety parameter determining processor 28 has the required software and/or computer programs stored in the memory (not shown) of the system control computer 24. To implement the method the software and/or computer programs is/are executed by the processor (not shown) of the system control computer 24.

In a first method step 100, position data of the patient 17 are acquired by the position data acquisition detector 31, in particular by the first camera 32 and/or the second camera 33. For this purpose, the patient 17 is already positioned on the patient-positioning device 18, in particular on the examination table 19. In a subsequent method step 101 the acquired position data are transmitted from the position data acquisition detector 31 to the safety parameter determining processor 28 by a data transmission unit (not shown).

In a further, subsequent method step 102 the acquired position data are evaluated, and position information of the patient 17 is determined, by the safety parameter determining processor 28 using the acquired position data. The position information can represent a position and/or orientation of the patient 17 on the patient-positioning device 18, in particular on the examination table 19. The position information preferably represents a position of the patient 17 on the patient-positioning device 18, in particular on the examination table 19 of the patient-positioning device 18.

The patient information preferably represents a patient model that is calculated using the acquired position data by means of the safety parameter determining processor 28. Using the patient model, an image and/or a model of the patient 71 is created and a position and/or orientation and/or situation of the patient 17 on the patient-positioning device 18, in particular the examination table 19 of the patient-positioning device 18, is determined as precisely as possible. The patient model is determined by an Active Shape Model and/or a cylinder model by the safety parameter determining processor 28. A provisional patient model is iteratively adjusted in this connection until there is the best possible match with anatomy of the patient 17.

Using the position information of the patient 17, the patient-specific safety parameter is determined by the safety parameter determining processor 28 in a further method step 103. The patient-specific safety parameter preferably is a specific absorption rate. In this way the specific absorption rate for the medical imaging examination can be ascertained and/or determined on the basis of optimally precise patient data, in particular the determined patient models. Thus safety tolerances, which are conventionally used due to roughly estimated patient data and that increase the scanning time of the medical imaging examination, are not needed.

In addition to the specific absorption rate, the patient-specific safety parameter can be heat radiation on the patient 17 during the medical imaging examination. The heat radiation on the patient 17 is also dependent, inter alia, on the distance of the patient 17 from the enclosure 36 of the patient-receiving region 16 during the medical imaging examination. Heat irradiation on the patient 17 can also be dependent on the choice of sequence and/or further scanning parameters of the medical imaging examination.

A further patient-specific absorption parameter can be a collision probability of the patient 17 with the enclosure 36 of the patient-receiving region 16 when the examination table 19 is moved into the patient-receiving region 16. Data obtained by the first camera 32, which is arranged inside the patient-receiving region 16, can be used for this purpose. For a comparison, the safety parameter determining processor 28 compares an image of the patient 17 on the examination table 19 just before the examination table 19 is moved into the patient-receiving region 16, with an image of an empty patient-receiving region 16, and the collision probability can be ascertained therefrom. The empty patient-receiving region is preferably patient-free. The image of the empty patient-receiving region 16 can be stored in the memory of the system control computer 24, or have been acquired by the first camera 32.

In a subsequent, but optional, method step 104, at least one of the determined patient-specific safety parameters is depicted for a user by the depiction unit, so the user can always monitor the patient-specific safety parameter. Furthermore, at least one item of advice and/or at least one work instruction is depicted and/or otherwise presented by the depiction unit 26 for the user in the method step. The at least one item of advice and/or the at least one work instruction can be, for example, a safety warning if a limit value for a patient-specific safety parameter is exceeded, for example with respect to a possible collision of the patient 17 with the enclosure 36 of the patient-receiving region 16 and/or with respect to excessive heating of the patient 17 during the medical imaging examination, etc. Furthermore, the at least one item of advice or the at least one work instruction can also comprise a request for a work instruction, such as, for example, a repositioning of the patient 17 due to a potential risk of collision of the patient 17 when the patient 17 is moved into the patient-receiving region 16 and/or owing to excessive heating of the patient 17 due to an inadequate distance of the patient 17 from the enclosure 36 of the patient-receiving region 16.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining at least one patient-specific safety parameter for a medical imaging examination conducted on a patient by a medical imaging apparatus, said method comprising:
    with a position data acquisition detector, acquiring position data of the patient while the patient is situated on a patient-positioning device of the medical imaging apparatus;
    transmitting the acquired position data to a safety parameter determining processor;
    in said safety parameter determining processor, evaluating the acquired position data to obtain position information of the patient;
    in said safety parameter determining processor, generating a patient model based on said position information of the patient, the patient model being an Active Shape Model; and
    in said safety parameter determining processor, determining a patient-specific safety parameter using the patient model, and making the patient-specific safety parameter available in electronic form from the safety parameter determining processor.

2. A method as claimed in claim 1 comprising determining said patient-specific safety parameter as a specific absorption rate of the patient.

3. A method as claimed in claim 1 wherein said at least one patient-specific safety parameter comprises heat radiation on the patient during said medical imaging examination.

4. A method as claimed in claim 1 wherein said at least one patient-specific safety parameter comprises a probability of collision of the patient with an enclosure of a patient-receiving region of said medical imaging apparatus.

5. A method as claimed in claim 1 comprising visually depicting a representation of said patient-specific parameter at a depiction unit in communication with said safety parameter determining processor.

6. A method as claimed in claim 5 comprising also presenting a representation of at least one of a work instruction and advice for conducting the medical imaging examination, at said depiction unit.

7. A method as claimed in claim 1 wherein said position data acquisition detector comprises at least one camera situated outside of a patient-receiving region that is at least partially surrounded by a medical data acquisition scanner of said medical imaging apparatus.

8. A method as claimed in claim 1 wherein said position data acquisition detector comprises at least one camera situated inside of a patient-receiving region that is at least partially surrounded by a medical data acquisition scanner of said medical imaging apparatus.

9. A method as claimed in claim 1 wherein said position data acquisition detector comprises:
at least one camera situated outside of a patient-receiving region that is at least partially surrounded by a medical data acquisition scanner of said medical imaging apparatus; and
at least one camera situated inside of said patient-receiving region that is at least partially surrounded by said medical data acquisition scanner.

10. A method as claimed in claim 1 wherein generating the patient model comprises:
generating a provisional patient model based on the position information of the patient; and
iteratively adjusting the provisional patient model to generate the patient model.

11. A method as claimed in claim 1 wherein the Active Shape Model comprises multiple mutually connected points corresponding to a shape, a profile, and/or a surface image of the patient.

12. A method as claimed in claim 1 wherein the generating the patient model comprises:
incorporating a shape of the patient and/or a profile of the patient into the position data to determine a surface image of the patient; and
iteratively adjusting individual points of the patient model to form edges in the surface image.

13. A medical imaging apparatus comprising:
a medical data acquisition scanner having a patient-positioning device;
a safety parameter determining processor; and
a position data acquisition detector that is configured to acquire position data of the patient while the patient is situated on said patient-positioning;
device, and to transmit the acquired position data to said safety parameter determining processor, wherein the safety parameter determining processor is configured to:
evaluate the acquired position data to obtain position information of the patient;
generate a patient model based on said position information of the patient, the patient model being an Active Shape Model; and
determine a patient-specific safety parameter using the patient model, and to make the patient-specific safety parameter available in electronic form from the safety parameter determining processor.

14. An apparatus as claimed in claim 13 wherein said position data acquisition detector comprises at least one camera situated outside of a patient-receiving region that is at least partially surrounded by said medical data acquisition scanner.

15. An apparatus as claimed in claim 13 wherein said position data acquisition detector comprises at least one camera selected from the group consisting of 2D cameras and 3D cameras.

16. A non-transitory, computer-readable data storage medium encoded with programming instructions, said programming instructions being loaded into a control computer of a medical imaging apparatus that comprises a position data acquisition detector and a safety parameter determining processor, said storage medium being encoded with programming instructions that cause said a position data acquisition detector and said safety parameter determining processor to:
with said position data acquisition detector, acquire position data of the patient while the patient is situated on a patient-positioning device of the medical imaging apparatus;
transmit the acquired position data to the safety parameter determining processor;
in said safety parameter determining processor, evaluate the acquired position data to obtain position information of the patient;
in said safety parameter determining processor, generate a patient model based on said position information of the patient, the patient model being an Active Shape Model; and
in said safety parameter determining processor, determine a patient-specific safety parameter using the patient model, and make the patient-specific safety parameter available in electronic form from the safety parameter determining processor.

* * * * *